United States Patent
Beylich et al.

(10) Patent No.: US 6,853,203 B2
(45) Date of Patent: Feb. 8, 2005

(54) OIL QUALITY MEASUREMENT DEVICE

(75) Inventors: Markus Beylich, Ludwigsburg (DE); Andreas Franz, Kornwestheim (DE)

(73) Assignee: Mann & Hummel GmbH, Ludwigsburg (DE)

(*) Notice: Subject to any disclaimer, the term of this patent is extended or adjusted under 35 U.S.C. 154(b) by 0 days.

(21) Appl. No.: 10/373,654

(22) Filed: Feb. 26, 2003

(65) Prior Publication Data

US 2003/0179002 A1 Sep. 25, 2003

(30) Foreign Application Priority Data

Feb. 27, 2002 (DE) .......................... 102 08 600

(51) Int. Cl.⁷ .............................................. G01R 27/08
(52) U.S. Cl. ...................... 324/698; 324/658; 324/691
(58) Field of Search ........................... 73/53.05, 61.75; 123/573; 324/658, 663, 698, 61.41, 691; 356/70; 210/168; 340/591; 702/50

(56) References Cited

U.S. PATENT DOCUMENTS

| | | | |
|---|---|---|---|
| 4,791,374 A | 12/1988 | Yodice et al. ............... 324/439 |
| 5,604,441 A * | 2/1997 | Freese et al. ............... 324/663 |
| 6,170,318 B1 | 1/2001 | Lewis .......................... 702/30 |
| 6,278,281 B1 * | 8/2001 | Bauer et al. ................. 324/441 |
| 6,380,746 B1 * | 4/2002 | Polczynski et al. ......... 324/446 |
| 6,718,819 B2 * | 4/2004 | Schoess ...................... 73/53.05 |
| 6,746,610 B2 * | 6/2004 | Manz et al. ................. 210/689 |

FOREIGN PATENT DOCUMENTS

| | | |
|---|---|---|
| DE | 19708067 | 9/1998 |
| DE | 1091098 | 4/2001 |
| DE | 10000148 | 7/2001 |
| DE | 10025690 | 11/2001 |
| GB | 2306660 | 5/1997 |
| WO | 99/58965 | 11/1999 |

OTHER PUBLICATIONS

Search Report EP 02 10 2817, Jun. 2003.

* cited by examiner

Primary Examiner—N. Le
Assistant Examiner—Walter Benson
(74) Attorney, Agent, or Firm—Crowell & Moring LLP

(57) ABSTRACT

An oil quality measurement device for an oil circuit (1), which includes an oil condition sensor (2) and an analysis circuit (3). The oil condition sensor (2) is constructed as a capacitive or impedance spectroscopic sensor (4) and attached to the filter element (14) in such a way that, when the filter element (14) is replaced, the oil condition sensor (2) is also automatically replaced.

5 Claims, 4 Drawing Sheets

OIL QUALITY MEASUREMENT DEVICE

BACKGROUND OF THE INVENTION

The present invention relates to an oil quality measurement device for an oil circuit.

The reliable operation of an oil circuit for lubricating an internal combustion engine in a motor vehicle or a hydraulic installation, for example, requires good oil quality. In the course of operation of an oil circuit, the oil quality may deteriorate, for example, due to dirt contamination, decomposition, water absorption, or the like. In lubricant oil circuits of internal combustion engines, soot particles, abraded metal, and even fuel, among other things, enter the oil in an undesired way and reduce its lubricating ability.

To maintain a specific oil quality over a predetermined cycle, an oil filter, which serves to filter contaminants which arise out of the oil, is arranged in the oil circuit. Particularly during the operation of diesel motors, corrosive acids may arise in the oil, for whose neutralization appropriate metallic materials are positioned in the oil filter. Unfavorable operating parameters, such as frequently performing a cold start, may lead to premature deterioration of the oil quality, even within the predetermined oil change interval. As a consequence, increased wear or even damage to the hydraulic installation and/or drive motor may occur.

To avoid these problems, U.S. Pat. No. 4,791,374 discloses an oil circuit in which an oil condition sensor is provided for measuring the oil quality. If the measured parameters deviate from a target range, deterioration of the oil quality may be recognized early and an oil change can be initiated. High requirements are set on the quality and particularly the service life of the oil condition sensor, which, among other things, makes the measurement device expensive and uneconomical.

SUMMARY OF THE INVENTION

It is an object of the present invention to provide an improved oil quality measuring device for an oil circuit.

Another object of the invention is to provide an oil quality measuring device for an oil circuit which is highly reliable.

A further object of the invention is to provide an oil quality measuring device which is economical and cost-effective.

These and other objects are achieved in accordance with the present invention by providing an oil quality measurement device for an oil circuit, comprising an oil condition sensor electrically connected to an analysis circuit, wherein the oil condition sensor is constructed as a capacitive or impedance spectroscopic sensor and is attached to a filter element such that the oil condition sensor is also replaced when the filter element is replaced.

For this purpose, an oil quality measurement device for an oil circuit, having an oil condition sensor and an analysis circuit, is proposed. The oil condition sensor is constructed as a capacitive or impedance spectroscopic sensor. This sensor is arranged in an oil filter of the oil circuit and is automatically replaceable as a unit together with the filter element. The analysis circuit is fixedly mounted on a housing of a component of the oil circuit, separate from the oil filter. By providing such a sensor together with an analysis circuit, it is possible to reliably measure a variety of parameters for detecting the oil quality.

The sensor may be constructed simply and cost-effectively in this case without impairing its reliability. Regular replacement of the sensor together with the filter element ensures the reliability of the measurement device as a whole over a long service life. The analysis circuit, which is fixedly arranged on the oil circuit outside the oil filter, is protected from the influence of the oil and may be designed at low cost for a long service life extending over multiple oil change intervals or even throughout the overall service life of the system.

Especially if the oil condition sensor and the analysis circuit are designed for measurement by impedance spectroscopy, high system reliability can be achieved at low cost. In impedance spectroscopy, the dielectric constants, the loss angle, and the conductivity of the oil are determined as a function of a measurement voltage frequency applied to the capacitive sensor.

From the viewpoint of measurement technology, the oil to be measured, which has multiple components, some of which are harmful, constitutes a complex resistor. A real part and an imaginary part of its impedance spectrum may be determined as a function of the measurement frequency in the manner described above. Each contaminant component in the oil has its own specific individual conductivity, which may be identified in the measured impedance spectrum. Thus, the oil to be tested may be checked in regard to the content of multiple contaminants using a single measurement device, and particularly using one single, simply constructed capacitive sensor in the oil filter.

The parts lubricated and/or moved in the oil circuit are reliably protected by monitoring the oil quality. Through monitoring of the oil contents, protection for the filter element is also provided, since an acid component in the oil, which reduces the useful life of the filter element, may be detected in a timely manner.

Integration of the sensor into the oil filter such that the filter and sensor are replaceable together helps to protect the sensor element itself from extended exposure to corrosive acids in the oil, for example, in diesel motors.

In one advantageous embodiment, a filter housing may be screwed into a filter receptacle. Electrical contact between the oil condition sensor and the analysis circuit is achieved via annular ring contacts. A reliable, planar contact is provided independently of the angular position of the filter element. Alternatively or in combination with this, a connecting plug may be provided, which is preferably arranged outside the oil filter housing and is therefore protected from corrosive influences.

By arranging the analysis circuit directly on the filter receptacle of the oil filter, short electric paths between the sensor and the analysis circuit are provided, which contributes to increasing the measurement precision. In such a case, the analysis circuit may advantageously be positioned in a separate housing, which is attached to the filter receptacle. In this way, the analysis circuit may be easily replaced in case of damage.

Modular oil filters of otherwise identical construction may be alternately made and supplied with and without an oil quality measurement device. It is also possible to retrofit an existing oil circuit with an oil condition sensor and an analysis circuit.

It has been found advantageous to position the oil condition sensor on the filtered oil side of the oil filter in order to increase the measurement precision. The concentration of foreign materials in the oil is comparatively low at this location and relatively free of suspended particles. These factors favor the acquisition of a precise and accurate measurement result.

In one advantageous embodiment, the oil condition sensor is integrated into an end plate of the filter element. The end plate is contacted by a good flow of the oil to be checked and thus the end plate offers a suitable location for precise measurement. When manufactured as a separate single part, it avoids the need for structural changes to the remaining components of the oil filter.

To increase the precision of the measured result, it has been found advantageous to construct the sensor with the greatest possible geometric extent or measurement length. For this purpose, it is advantageous to use a spiral-shaped or meandering arrangement, for example, of an electrically conductive measurement wire, metal strip, or the like, as a result of which a large overall measurement length may be housed in a small installation space.

In an advantageous embodiment in which the oil filter includes a substantially cylindrical supporting body and a filter element which encloses the supporting body, the oil condition sensor may be constructed as a cylindrical hollow body and may be arranged between the support body and the filter element. Due to the resulting support of the condition sensor on all sides, the mechanical stress on the condition sensor remains low. At the same time, there is a good flow of oil around the sensor, which contributes to increasing the measurement precision.

In an advantageous refinement of this embodiment, the support body of the oil filter is itself constructed as the oil condition sensor. This contributes to reducing the number of parts and the complexity of the system.

Particularly in oil filters in which only the filter element is replaced as an individual part, it may be advantageous to attach the oil condition sensor permanently to the filter element. This assures that the sensor will also be replaced when the filter is changed and prevents undesired extended operation of the sensor beyond its constructively predetermined service life.

BRIEF DESCRIPTION OF THE DRAWINGS

The invention will be described in further detail hereinafter with reference to illustrative preferred embodiments shown in the accompanying drawing figures, in which.

DETAILED DESCRIPTION OF PREFERRED EMBODIMENTS

Figure 1:
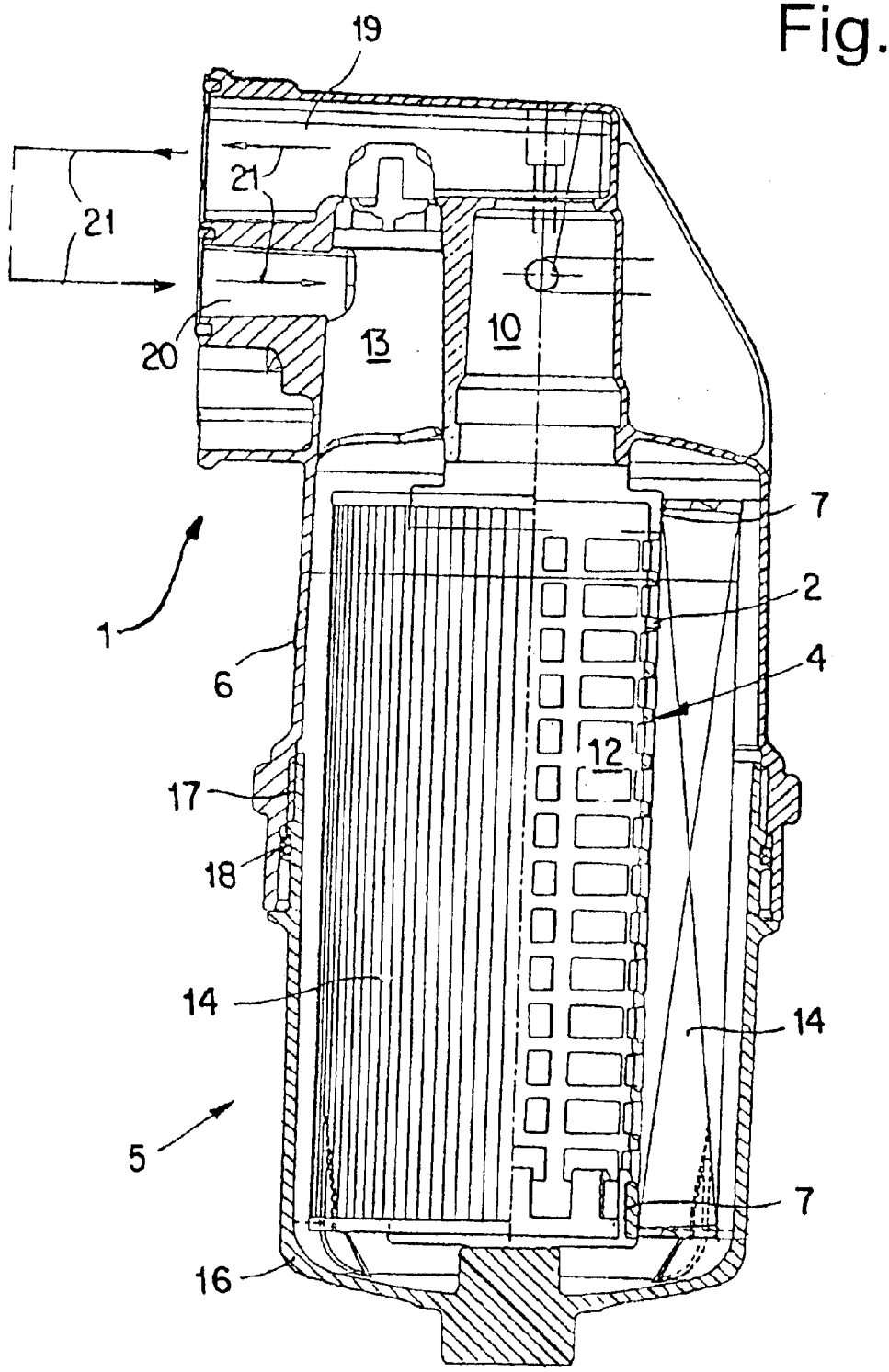
FIG. 1 is a partially sectioned view of an oil filter for a symbolically illustrated oil circuit having a foraminous support constructed as an oil condition sensor.

FIG. 1 shows a sectional illustration of an oil filter 5 of a schematically outlined oil circuit 1, using the example of a lubricant oil circuit for a truck diesel motor. Comparable arrangements may also be provided for lubricant oil circuits in passenger vehicles, for gear oil circuits, and for hydraulic oil circuits.

In the oil circuit 1, an oil filter 5 is provided, which, in the illustrative embodiment shown, comprises a filter housing 16 screwed into a filter receptacle 6. A cylindrical, perforate or foraminous support body 12 and a filter element 14, which is also cylindrical and which encloses the support body 12, are positioned in the filter housing 16. The support body 12 and the filter element 14 are held in the axial direction between an end wall of the filter housing 16 and the filter receptacle 6. The filter housing 16 may be screwed into the filter receptacle 6 using a thread 17 and is sealed in relation to the filter receptacle 6 via a circumferential O-ring 18.

The flow direction of the oil in the oil circuit 1 is indicated by the arrow 21, according to which the oil is conducted through an inlet 20 to an inflow side 13 of the oil filter 5. In the oil filter 5, the oil flows radially through the filter element 14 from the outside to the inside. The cylindrical filter element 14 is enabled to withstand the resulting pressure differential, which acts in a radially inward direction, as a result of the supporting effect of support body 12. The filtered oil side 10 of the oil filter 5 is radially inside the filter element 14. In order to discharge the filtered oil, the inside of the filter element is in fluid communication with an outlet 19 in the filter receptacle 6.

In the illustrative embodiment shown in FIG. 1, the support body 12 is constructed as an oil condition sensor 2 in the form of a capacitive sensor 4 and is therefore on the filtered oil side 10 of the oil filter 5. In order to provide electrical contact between the sensors 2 and 4 and an analysis circuit 3, an annular ring contact 7 is provided in the vicinity of each of the end faces of the supporting body 12. Analysis circuit 3 is described in greater detail in connection with FIG. 3.

Figure 2:
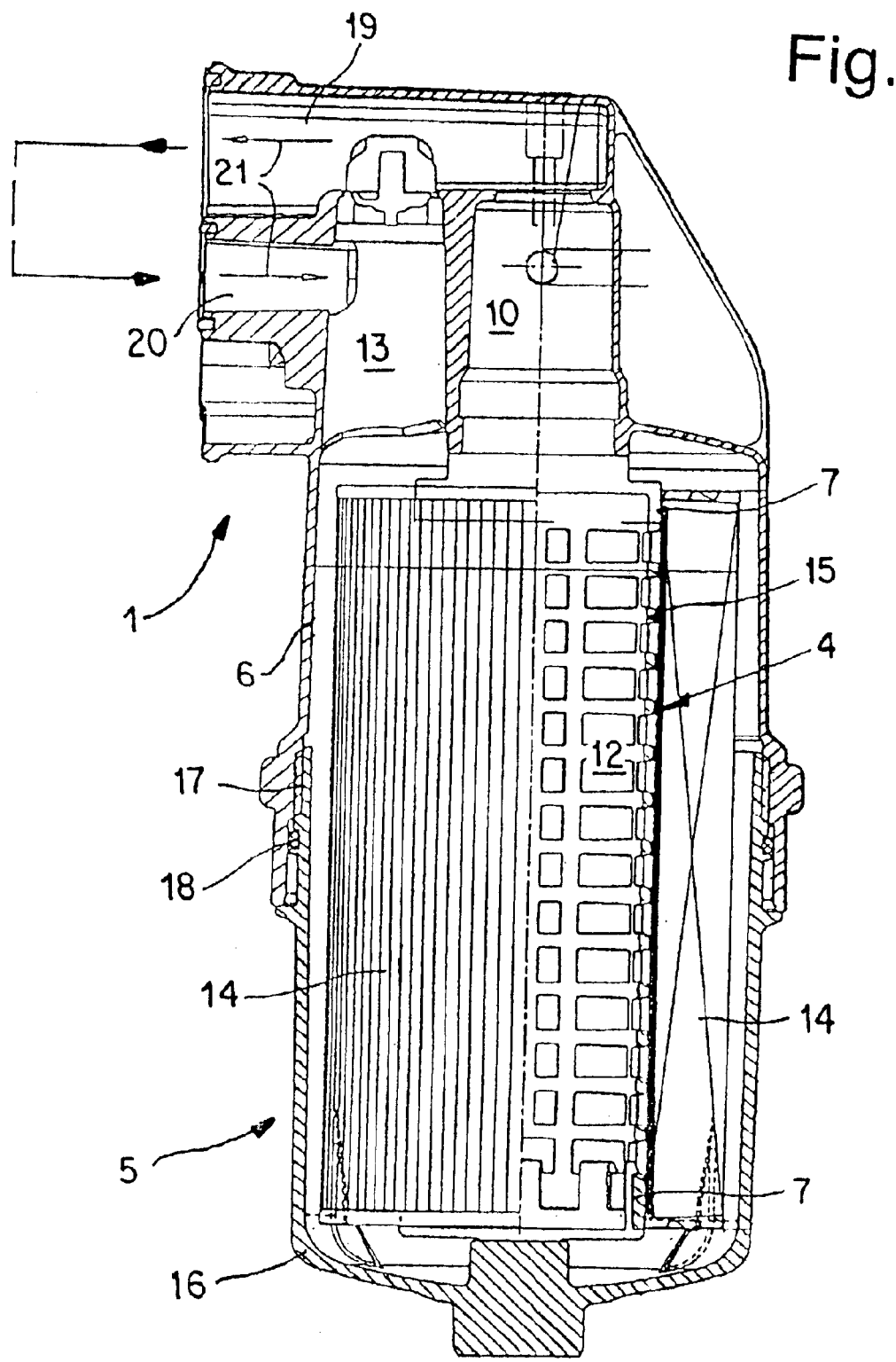
FIG. 2 is a partially sectioned view of a variant of the arrangement shown in FIG. 1 having an oil condition sensor constructed as a cylindrical hollow body arranged between the support body and the filter element.

FIG. 2 shows a variant of the arrangement shown in FIG. 1, in which the capacitive sensor 4 is constructed as a cylindrical hollow body 15 and is positioned between the support body 12 and the filter element 14. The remaining features and reference numbers of the arrangement shown in FIG. 2 correspond to those shown in FIG. 1.

The capacitive sensor 4 shown in FIGS. 1 and 2 may be constructed from stamped or etched sheet metal, from wound or braided or otherwise shaped wire, as an etched circuit board, or the like. In this case, the sensor 4 is made of an electrically conductive material, which advantageously has a high corrosion resistance. Stainless steel, titanium and carbon fibers have been shown to be suitable sensor materials.

Figure 3:
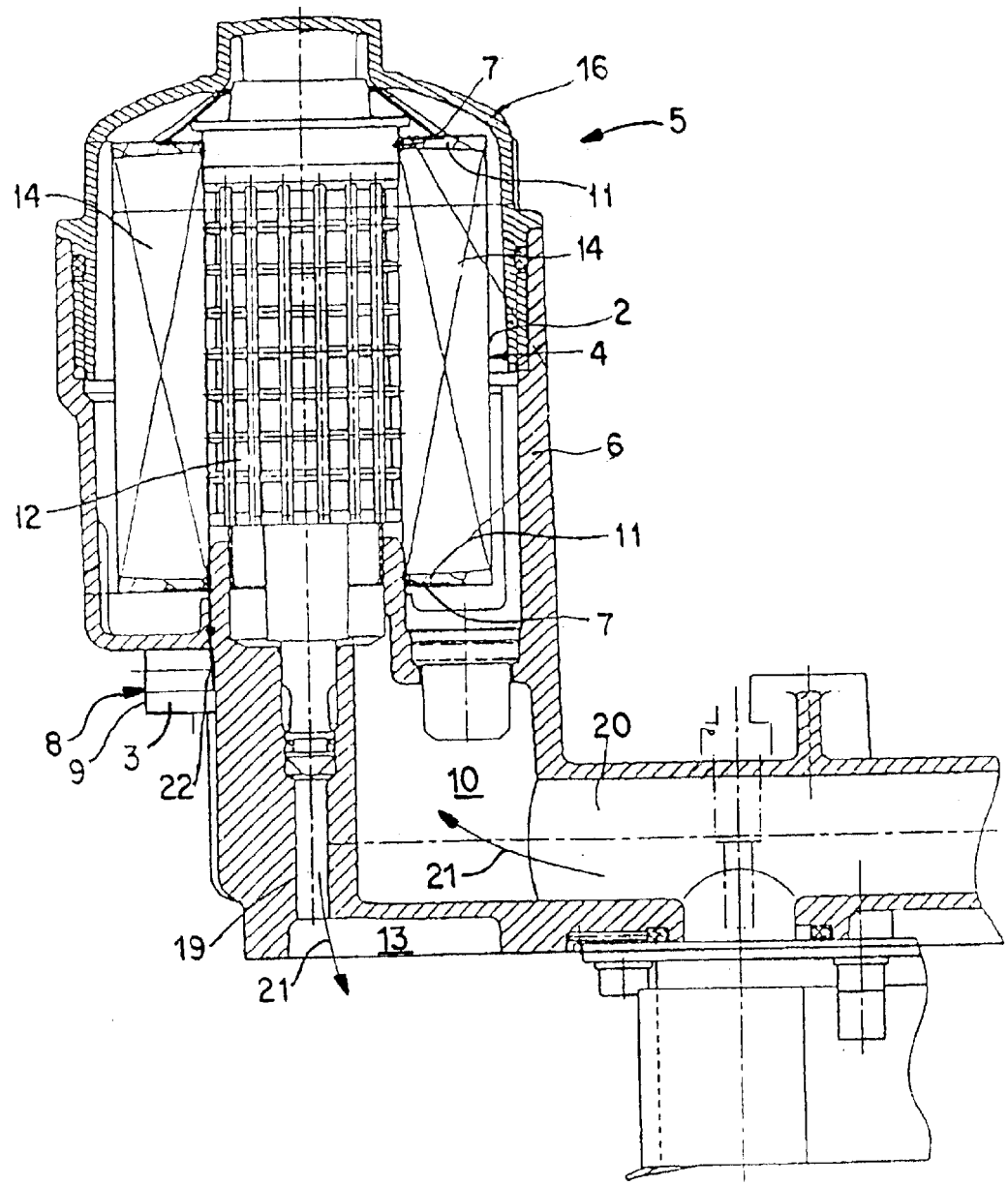
FIG. 3 is a partially sectioned view of a further oil filter arrangement having a wire-like oil condition sensor permanently attached to the filter element.

FIG. 3 shows a further arrangement of a filter 5 comprising a cylindrical support body 12 and a likewise cylindrical filter element 14, which are held in a filter housing 16 and a filter receptacle 6. An end plate 11 is provided at each axial end of the filter element 14. The oil condition sensor 2 is constructed as a capacitive sensor 4 and is permanently attached to the radially outer side of the replaceable filter body 14.

An analysis circuit 3 is arranged in a separate housing 9 on the outside of the filter receptacle 6 and fixedly mounted on the filter receptacle 6. A combination of annular contacts 7, a line 22 which extends through the filter receptacle 6 from the outside to the inside, and a connector plug 8 is provided to establish electrical contact between the sensors 2 and 4 and the analysis circuit 3. The analysis circuit 3 in the separate housing 9 may be replaced as needed by releasing the plug connector 8.

It may also be advantageous to have an arrangement in which the analysis circuit 3 is integrated into the filter receptacle 6. In the illustrative embodiment shown in FIGS. 1 to 3, the oil filter 5 and/or the sensors 2, 4 are intended to be replaced together with the filter element 14. It may also be advantageous to replace the sensors together with a module comprised of the filter element 14 and the filter housing 16.

Figure 4:
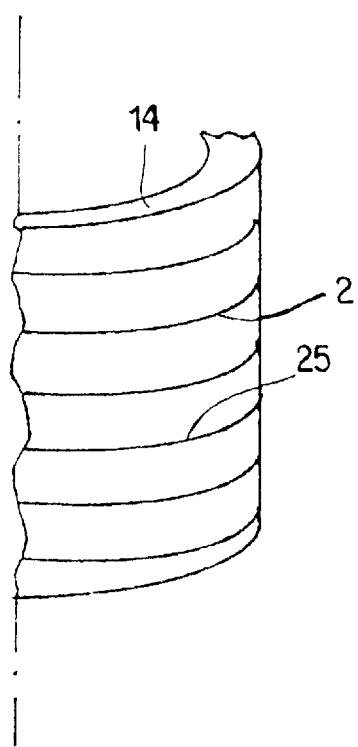
FIG. 4 is a diagrammatical illustration of details of a helically wound wire forming an oil condition sensor.

FIG. 4 shows a schematic perspective illustration of a detail from the filter element 14 shown in FIG. 3. In this case, the oil condition sensor 2 is constructed as a helically wound stainless steel wire 25, and wrapped around the radially outer side of the filter element 14. It may be advantageous to interweave, adhesively bond, rivet, or otherwise fixedly attach the oil condition sensor 2 to the radial outside of the filter body 14. Likewise, it may be advantageous to attach the oil condition sensor 2 to the radial inside of the filter body 14.

Figure 5:
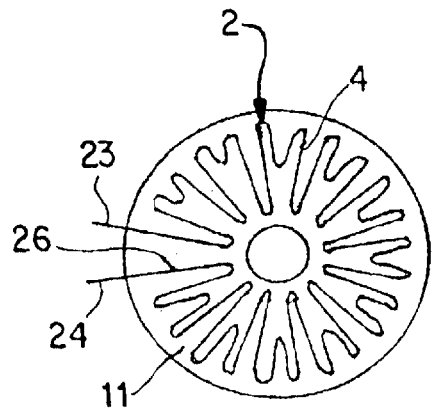
FIG. 5 is a schematic illustration of a meandering oil condition sensor attached to an end plate of the filter element.

FIG. 5 shows a schematic illustration of a construction of the end plate 11 shown in FIG. 3, in which the oil condition sensor 2 is integrated into the end plate 11. The oil condition sensor 2, which is constructed as a capacitive sensor 4, extends as a meandering conductor track 26 on the surface of the end plate 11 and is provided with two radially outwardly extending connector contacts 23 and 24.

Figure 6:
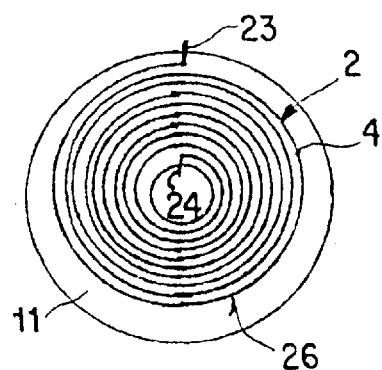
FIG. 6 is a schematic illustration of an alternate oil condition sensor configuration also attached to an end plate of the filter element.

In the variant of the arrangement shown in FIG. 5 which is shown in FIG. 6, the conductor track 26 for forming the sensors 2, 4 has a spiral-shaped course on the surface of the end plate 11. Respective radially inner and outer contacts 23 and 24 are provided to establish electrical connections to each of the sensors 2, 4.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. An oil quality measurement device for an oil circuit, comprising an oil condition sensor electrically connected to an analysis circuit, wherein the oil condition sensor is constructed as a capacitive or impedance spectroscopic sensor and is attached to a filter element such that the oil condition sensor is also replaced when the filter element is replaced, wherein the analysis circuit is disposed on a filter receptacle for an oil filter which comprises said filter element, and wherein the filter element is enclosed by a filter housing which is screwed into the filter receptacle, and annular contacts are provided on the filter element for establishing electrical contact between the oil condition sensor and the analysis circuit.

2. An oil quality measurement device for an oil circuit, comprising an oil condition sensor electrically connected to an analysis circuit, wherein the oil condition sensor is constructed as a capacitive or impedance spectroscopic sensor and is attached to a filter element such that the oil condition sensor is also replaced when the filter element is replaced, wherein the oil condition sensor is arranged on a filtered oil side of the filter element.

3. An oil quality measurement device for an oil circuit, comprising an oil condition sensor electrically connected to an analysis circuit, wherein the oil condition sensor is constructed as a capacitive or impedance spectroscopic sensor and is attached to a filter element such that the oil condition sensor is also replaced when the filter element is replaced, wherein the oil condition sensor is integrated into an end plate of an oil filter which comprises the filter element, wherein the end plate contacts an end of the filter element.

4. An oil quality measurement device for an oil circuit, comprising an oil condition sensor electrically connected to an analysis circuit, wherein the oil condition sensor is constructed as a capacitive or impedance spectroscopic sensor and is attached to a filter element such that the oil condition sensor is also replaced when the filter element is replaced, wherein the filter element annularly surrounds a substantially cylindrical foraminous support body, and the oil condition sensor is constructed as a hollow body and is arranged between the filter element and the support body.

5. An oil quality measurement device for an oil circuit, comprising an oil condition sensor electrically connected to an analysis circuit, wherein the oil condition sensor is constructed as a capacitive or impedance spectroscopic sensor and is attached to a filter element such that the oil condition sensor is also replaced when the filter element is replaced, wherein the filter element annularly surrounds a substantially cylindrical support body, and said support body is constructed as the oil condition sensor.

* * * * *